US008658660B2

(12) United States Patent
Boebel et al.

(10) Patent No.: US 8,658,660 B2
(45) Date of Patent: Feb. 25, 2014

(54) 5-FLUORO-4-IMINO-3,4-DIHYDROPYRIMIDIN-2-(1H)-ONES DERIVATIVES

(75) Inventors: Timothy A. Boebel, Indianapolis, IN (US); Beth Lorsbach, Indianapolis, IN (US); W. John Owen, Carmel, IN (US); Michael T. Sullenberger, Westfield, IN (US); Jeffery D. Webster, New Palestine, IN (US); Chenglin Yao, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/586,450

(22) Filed: Aug. 15, 2012

(65) Prior Publication Data

US 2013/0045984 A1 Feb. 21, 2013

Related U.S. Application Data

(60) Provisional application No. 61/524,506, filed on Aug. 17, 2011.

(51) Int. Cl.
*A61K 31/505* (2006.01)

(52) U.S. Cl.
USPC .......................................................... 514/274

(58) Field of Classification Search
None
See application file for complete search history.

(56) References Cited

U.S. PATENT DOCUMENTS

| 3,309,359 | A | | 3/1967 | Duschinsky et al. |
| 3,368,938 | A | | 2/1968 | Berger et al. |
| 3,635,977 | A | * | 1/1972 | Lutz et al. ..................... 544/309 |
| 3,868,373 | A | | 2/1975 | Hoffer |
| 4,845,081 | A | | 7/1989 | Sloan |
| 4,996,208 | A | | 2/1991 | Lindner et al. |
| 5,962,489 | A | | 10/1999 | Mueller et al. |
| 6,066,638 | A | | 5/2000 | Bereznak et al. |
| 6,617,330 | B2 | | 9/2003 | Walter |
| 7,914,799 | B2 | | 3/2011 | Jira et al. |
| 2003/0039667 | A1 | | 2/2003 | Jira et al. |
| 2008/0004253 | A1 | | 1/2008 | Branstetter et al. |
| 2008/0269238 | A1 | | 10/2008 | Sugihara et al. |
| 2009/0203647 | A1 | | 8/2009 | Benko et al. |
| 2010/0022538 | A1 | | 1/2010 | Boebel et al. |
| 2011/0034493 | A1 | | 2/2011 | Boebel et al. |
| 2011/0082162 | A1 | * | 4/2011 | Lorsbach et al. ............. 514/274 |

FOREIGN PATENT DOCUMENTS

| EP | 0102908 A1 | 3/1984 |
| EP | 0139613 A1 | 5/1985 |
| EP | 0332579 A2 | 9/1989 |
| EP | 0877022 B1 | 4/2003 |
| GB | 1461184 A | 1/1977 |
| JP | 6001793 A | 1/1994 |
| WO | WO9733890 A1 | 9/1997 |
| WO | WO2009/094442 A2 | 7/2009 |
| WO | WO2010047866 A2 | 4/2010 |
| WO | WO2010085377 A2 | 7/2010 |

OTHER PUBLICATIONS

Woese, C., et al, Towards a natural system of organisms: Proposal for the domains Archaea, Bacteria, and Eucarya, Proc. Natl. Acad. Sci., vol. 87, pp. 4576-4579.*
Liang, Ying, et al., A facile synthesis and herbicial activities of novel fluorine-containing thiazolo[4,5-e]ryimidin-7(6H)-ones, Journal of Fluorine Chemistry: 128 (2007) 879-884.*
International Search Report and Written Opinion for PCT/US2012/050930, Oct. 15, 2012.
International Search Report for PCT/US2010/044579, Sep. 21, 2010.
Chiacchio U, et al., Enantioselective Syntheses and Cytotoxicity of N,O-Nucleosides. Journal of Medicinal Chemistry, Jan. 1, 2003, vol. 46, pp. 3696-3702.
Morris J Robins et al., A direct synthesis of 5-fluorocytosine and its nucleosides using trifluoromethyl hypofluorite. Journal of the Chemical Society, Chemical Communications, No. 1, Jan. 1, 1972, p. 18.
Arthur F. Lewis et al. Synthesis and in vitro anti-human cytomegalovirus (hcmv) activity of certain alkenyl substituted cytosines and 5-halocytosines. Journal of Heterocyclic Chemistry, Sep. 1, 1995, vol. 32, Nr:5, pp. 1513-1515.
Kulikowski et al. Methylation and tautomerism of 5-fluorocytosine nucleosides and their analogues. Journal Nucleic Acids Research, Jan. 1, 1978, vol. 4, pp. S7-S10.
Supplemental European Search Report for EP10807172 (PCT/US2010/044579), Dec. 7, 2012.
International Search Report for PCT/US2010/044592, Sep. 21, 2010.
International Search Report for PCT/US2009/031683, Jan. 22, 2009.
Jaworski et al. Infrared spectra and tautomerism of 5-fluorocytosine, 5-bromocytosine and 5-iodocytosine. Matrix isolation and theoretical ab initio studies. Journal of Molecular Structure, Jan. 1, 1990, vol. 223, pp. 63-92.
Gabriella et al. Some 5-fluorosulfanilamidopyrimidines. Gazzetta Chimica Italiana, Jan. 1, 1963, vol. 93, Nr:10, pp. 1268-1278.
Zhang et al., Improved method for synthesis of 5-fluorocytosine (5-FC). CAPLUS Abstract 111:134074 (1989).
International Search Report for PCT/US2011/020351, Mar. 14, 2011.
Liang et al., A facile synthesis and herbicidal activities of novel fluorine-containing thiazolo[4,5-d] pyrimidin-7(6H)-ones. Journal of Fluorine Chemistry [online], Jul. 2007, vol. 128, Iss. 7, pp. 879-884.
Bera et al., Nucleosides with furanyl scaffolds. Tetrahedron, Jun. 10, 2002, vol. 58, Nr:24, pp. 4865-4871.
Duschinsky et al., Cytosine derivatives. CAPLUS Abstract 61:18527, 1964.
International Search Report for PCT/US2010/044588, Oct. 1, 2010.
International Search Report for PCT/US2012/050931, Oct. 9, 2012.
Waring, M J, Defining optimum lipophilicity and molecular weight ranges for drug candidates—Molecular weight dependent lower logD limits based on permeability. Bioorganic & Medical Chemistry Letters, May 15, 2009, vol. 19, Nr: 10, pp. 2844-2851.
International Search Report for PCT/US2010/060792, Apr. 22, 2011.
International Search Report for PCT/US2010/044576, Sep. 23, 2010.
Duschinsky et al., Nucleosides. XXXIII. N4-Acylated 5-Fluorocytosines and a Direct Synthesis of 5-Fluoro-2'-deoxycytidine. Journal of Medicinal Chemistry, Jul. 1, 1966, vol. 9, Nr:4, pp. 566-572.

* cited by examiner

*Primary Examiner* — San-Ming Hui
*Assistant Examiner* — Jeanmarie Calvillo
(74) *Attorney, Agent, or Firm* — C. W. Arnett; Faegre Baker Daniels, LLP

(57) ABSTRACT

This present disclosure is related to the field of 5-fluoro-4-imino-3-(substituted)-3,4-dihydropyrimidin-2(1H)ones and their derivatives and to the use of these compounds as fungicides.

4 Claims, No Drawings

5-FLUORO-4-IMINO-3,4-DIHYDROPYRIMIDIN-2-(1H)-ONES DERIVATIVES

CROSS REFERENCE TO RELATED APPLICATIONS

This application claims the benefit of U.S. Provisional Patent Application Ser. No. 61/524,506 filed Aug. 17, 2011, which is expressly incorporated by reference herein.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to 3-alkyl-5-fluoro-4-imino-3,4-dihydropyrimidin-2(1H)one compounds and their use as fungicides. The compounds of the present disclosure may offer protection against ascomycetes, basidiomycetes, deuteromycetes and oomycetes.

One embodiment of the present disclosure may include compounds of Formula I:

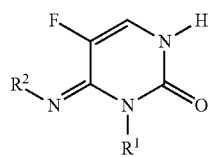

Formula I wherein $R^1$ is:
  $C_1$-$C_6$ alkyl optionally substituted with 1-3 $R^3$;
  $C_1$-$C_6$ alkenyl optionally substituted with 1-3 $R^3$;
  $C_3$-$C_6$ alkynyl optionally substituted with 1-3 $R^3$;
  phenyl or benzyl wherein each of the phenyl or the benzyl may be optionally substituted with 1-3 $R^4$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^4$,
  —(CHR$^5$)$_m$OR$^6$;
  —C(=O)R$^7$;
  —C(=S)R$^7$;
  —C(=O)OR$^7$;
  —C(=S)OR$^7$;
  —S(O)$_2$R$^7$;
  —(CHR$^5$)$_m$N(R$^8$)R$^9$;
  —C(=O)N(R$^8$)R$^9$; or
  —C(=S)N(R$^8$)R$^9$;
wherein m is an integer 1-3;
$R^2$ is:
  H; or
  $C_1$-$C_6$ alkyl optionally substituted with $R^3$;
$R^3$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, $C_3$-$C_6$ trialkylsilyl, or with a 5- or 6-membered saturated or unsaturated ring system, or with a 5-6 fused ring system, or with a 6-6 fused ring system each containing 1-3 heteroatoms wherein each ring may be optionally substituted with 1-3R;

$R^4$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_1$-$C_6$ alkylsulfonyl or $C_2$-$C_6$ alkylcarbonyl, nitro, hydroxyl, or cyano;

$R^5$ is H, $C_1$-$C_6$ alkyl, $C_1$-$C_6$ alkoxy, phenyl or benzyl wherein each of the benzyl or the phenyl may be optionally substituted with 1-3 $R^4$;

$R^6$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^4$, or with a 5- or 6-membered saturated or unsaturated ring system, or with 5-6 fused ring system, or with a 6-6 fused ring system each containing 1-3 heteroatoms wherein each ring may be optionally substituted with 1-3 $R^4$, biphenyl or naphthyl optionally substituted with 1-3 $R^4$;

$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^4$, or with a 5- or 6-membered saturated or unsaturated ring system, or with a 5-6 fused ring system, or 6-6 fused ring system each containing 1-3 heteroatoms wherein each ring may be optionally substituted with 1-3 $R^4$, biphenyl or naphthyl optionally substituted with 1-3 $R^4$;

$R^8$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^4$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^4$, biphenyl or naphthyl optionally substituted with 1-3 $R^4$; and $R^9$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl may be optionally substituted with 1-3 $R^4$;

alternatively $R^8$ and $R^9$ may be taken together to form a 5- or 6-membered saturated or unsaturated ring containing 1-3 heteroatoms wherein each ring may be optionally substituted with 1-3 $R^4$.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the step of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_{1-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "alkylthio" refers to an —S—R substituent.

The term "halothio" refers to a sulfur substituted with three or five F substituents.

The term "haloalkylthio" refers to an alkylthio, which is substituted with Cl, F, I, or Br or any combination thereof.

The term "alkylaminocarbonyl" refers to a —C(O)—N(H)—R substituent.

The term "trialkylsilyl" refers to —SiR$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —NR$_2$ substituent.

The term "alkoxyalkyl" refers to an alkoxy substitution on an alkyl.

The term "halogen" or "halo" refers to one or more halogen atoms, defined as F, Cl, Br, and I.

The term "nitro" refers to a —NO$_2$ substituent.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$)ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, flufiprole, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, niflutridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora beticola*), leaf spots of peanut (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1

Preparation of 5-fluoro-4-imino-3-methyl-3,4-dihydropyrimidin-2(1H)-one (1)

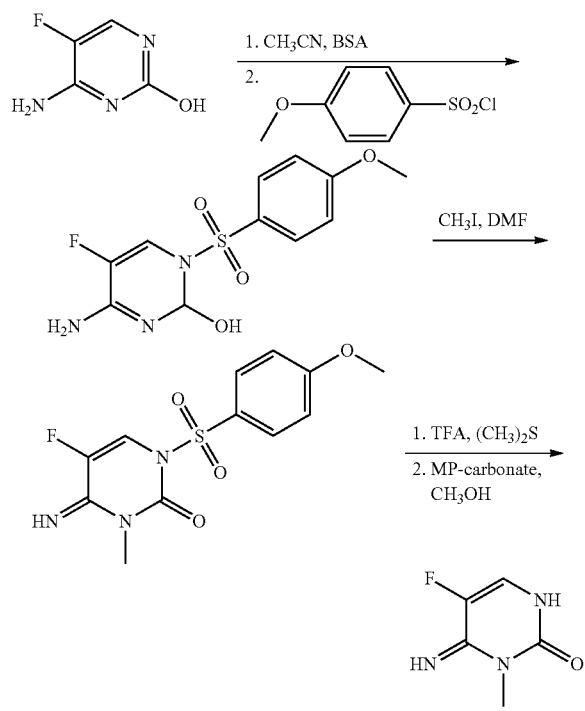

Step 1: 4-Amino-5-fluoro-1-(4-methoxyphenylsulfonyl)pyrimidin-2(1H)-one. To 4-amino-5-fluoro-pyrimidin-2-ol* (1.0 grams (g), 7.75 millimoles (mmol)) in acetonitrile (CH$_3$CN; 50 milliliters (mL)) was added bis-N,O-trimethylsilylacetamide (BSA; 5.7 mL, 23.3 mmol) and the mixture was heated at 70° C. for 1 hour (h) resulting in a clear solution. After cooling to room temperature, 4-methoxybenzene-1-sulfonyl chloride (1.8 g, 8.5 mmol) was added, and the mixture was stirred for 24 h. The solvent was evaporated and the residue was partitioned between ethyl acetate (EtOAc) and brine. The organic phase was dried over magnesium sulfate (MgSO$_4$), filtered, and evaporated to yield the product as a pale yellow solid (1.48 g, 64%): mp 182-5° C.; $^1$H NMR (300 MHz, CDCl$_3$) δ 8.40 (br s, 1H), 8.11 (d, J=5.9 Hz, 1H), 8.04-7.98 (m, 2H), 7.02-6.96 (m, 2H), 5.77 (br s, 1H), 3.88 (s, 3H); ESIMS m/z 300 ([M+H]$^+$). *4-Amino-5-fluoro-pyrimidin-2-ol can be purchased commercially.

Step 2: 5-Fluoro-4-imino-1-(4-methoxyphenylsulfonyl)-3-methyl-3,4-dihydropyrimidin-2(1H)-one. To a 8 mL screw capped vial were added 4-amino-5-fluoro-1-(4-methoxyphenylsulfonyl)-pyrimidin-2(1H)-one (0.293 g, 0.979 mmol), anhydrous potassium carbonate (K$_2$CO$_3$; 0.271 g, 1.96 mmol), and N,N-dimethylformamide (DMF; 4 mL), followed by iodomethane (CH$_3$I; 0.208 g, 1.47 mmol). The reaction vessel was sealed, and the reaction mixture was warmed to 60° C. and stirred for 4 h. The reaction mixture was cooled to room temperature, diluted with EtOAc (20 mL), and washed with water (H$_2$O; 3×10 mL). The organic phase was dried over MgSO$_4$, filtered, and the solvent evaporated under reduced pressure. Purification by flash chromatography (silica gel (SiO$_2$), EtOAc/Hexanes gradient) afforded the title compound as a pale yellow solid (36 mg, 12%): mp 158-162° C.; $^1$H NMR (400 MHz, DMSO-d$_6$) δ 8.01 (d, J=9.22 Hz, 2H), 7.74 (d, J=5.27 Hz, 1H), 7.04 (d, J=9.23 Hz, 2H), 3.90 (s, 3H), 3.31 (s, 3H); ESIMS m/z 314 ([M+H]$^+$).

Step 3: 5-Fluoro-4-imino-3-methyl-3,4-dihydropyrimidin-2(1H)-one (1). A 25 mL screw capped vial was charged with 5-fluoro-4-imino-1-(4-methoxyphenylsulfonyl)-3-methyl-3,4-dihydropyrimidin-2(1H)-one (80.4 mg, 0.257 mmol), trifluoroacetic acid (TFA; 16.0 mL, 215 mmol), and dimethylsulfide (94.0 μL, 1.28 mmol). The resulting solution was allowed to stir at room temperature for 5.5 h and was then concentrated to dryness by rotary evaporation at 30° C. The crude material was then dissolved in a minimal amount of methanol (CH$_3$OH; ~2 mL) and loaded onto a 5 g normal phase solid load Isco cartridge, rinsing the source vial with CH$_3$OH (3×1 mL). The solid cartridge was then dried under vacuum at room temperature. After drying, the product was purified by chromatography (4 g SiO$_2$ column; 0 to 30% CH$_3$OH in dichloromethane (CH$_2$Cl$_2$) gradient). The material thus obtained was determined to be the 4-methoxysulfonic acid salt of the desired product. The free base was obtained by dissolving the material in CH$_3$OH (4 mL), adding MP-carbonate resin (345 mg, 3.03 mmol/g, 4.0 equiv), and allowing to stir at room temperature. After stirring for 20 h, the solid resin was filtered off and rinsed with CH$_3$OH (3×1 mL). After concentration under high vacuum, 5-fluoro-4-imino-3-methyl-3,4-dihydropyrimidin-2(1H)-one (35.2 milligrams (mg), 96%) was obtained as a 95% pure white solid: mp 181-184° C.; $^1$H NMR (400 MHz, DMSO-d$_6$) δ 7.48 (d, J=4.1 Hz, 1H), 3.22 (s, 3H); $^{13}$C NMR (101 MHz, DMSO-d$_6$) δ 152.19 (s), 151.86 (d, J=27.3 Hz), 136.73 (d, J=221.0 Hz), 129.45 (d, J=26.0 Hz), 28.91 (s).

Example 2

Preparation of 5-fluoro-4-imino-3-(thiophen-2-ylmethyl)-3,4-dihydropyrimidin-2(1H)-one (2)

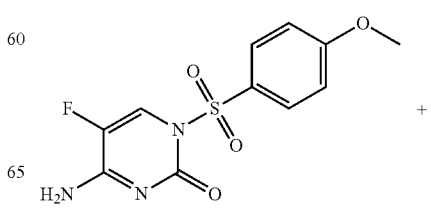

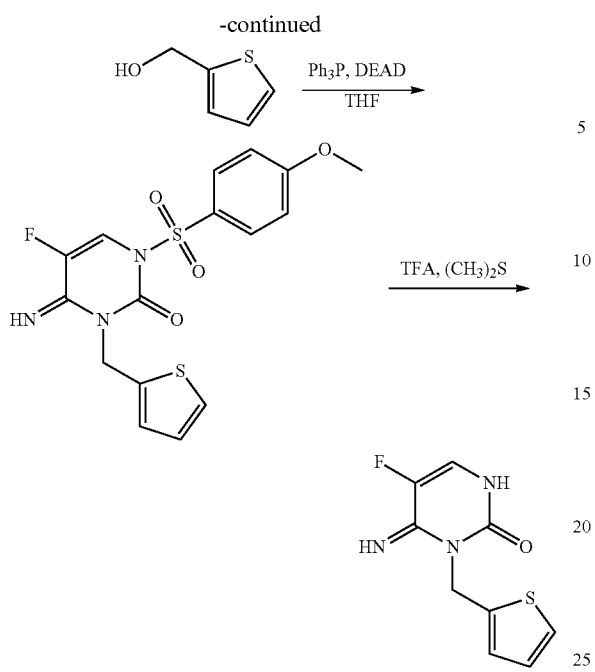

Step 1: 5-Fluoro-4-imino-1-((4-methoxyphenyl)sulfonyl)-3-(thiophen-2-ylmethyl)-3,4-dihydropyrimidin-2(1H)-one. To a 25 mL vial with magnetic stirring were added 4-amino-5-fluoro-1-((4-methoxyphenyl)sulfonyl)pyrimidin-2(1H)-one (150 mg, 0.501 mmol), thiophen-2-ylmethanol (172 mg, 1.504 mmol), triphenylphosphine (Ph$_3$P; 394 mg, 1.504 mmol) and dry tetrahydrofuran (THF; 4.204 mL). The reaction mixture was placed under nitrogen (N$_2$) atmosphere and cooled to ice-bath temperature. After cooling 10 minutes (min), diethylazodicarboxylate (DEAD; 0.238 mL, 1.504 mmol) was added dropwise and the mixture was allowed to warm to room temperature overnight. The reaction mixture was evaporated to dryness. The crude residue was purified on SiO$_2$ (EtOAc/hexanes gradient) to provide the title compound as a yellow-white wax (146 mg, 73.8%): $^1$H NMR (400 MHz, CDCl$_3$) δ 8.01 (d, J=9.1 Hz, 2H), 7.84 (d, J=1.8 Hz, 1H), 7.67 (d, J=5.5 Hz, 1H), 7.17 (dd, J=5.2, 1.2 Hz, 1H), 7.13 (d, J=3.5 Hz, 1H), 7.02 (d, J=9.1 Hz, 2H), 6.88 (dd, J=5.1, 3.5 Hz, 1H), 5.28 (s, 2H), 3.91 (s, 3H);. UV (CH$_2$Cl$_2$) λ$_{max}$: 259 nm; ESIMS m/z 396.5 ([M+H]$^+$).

Step 2: 5-Fluoro-4-imino-3-(thiophen-2-ylmethyl)-3,4-dihydropyrimidin-2(1H)-one (2). To a magnetically stirred mixture of 5-fluoro-4-imino-1-((4-methoxyphenyl)sulfonyl)-3-(thiophen-2-ylmethyl)-3,4-dihydropyrimidin-2(1H)-one (130 mg, 0.329 mmol) in dry TFA (2.529 mL) was added dimethyl sulfide (0.122 mL, 1.64 mmol) in a dry 25 mL vial under Argon atmosphere. The reaction mixture was stirred at 23° C. for 16 h. The reaction mixture was evaporated to dryness and the crude residue was diluted with ice-water and aqueous saturated sodium bicarbonate solution and extracted with CH$_2$Cl$_2$ (2×). The layers were separated, the combined organic extracts were evaporated, and the crude residue was purified on SiO$_2$ (EtOAc/CH$_2$Cl$_2$ gradient) to afford the title compound as an off-white wax (15 mg, 19.2%): $^1$H NMR (400 MHz, CDCl$_3$+D$_2$O) δ 7.22 (br d, J=3.4 Hz, 1H), 7.21 (dd, J=5.2, 1.1 Hz, 1H), 6.94 (dd, J=5.1, 3.5 Hz, 1H), 6.72 (d, J=4.3 Hz, 1H), 5.38 (s, 2H); $^{13}$C NMR (101 MHz, CDCl$_3$) δ 152.48 (d, J=30.5 Hz), 151.06 (s), 138.17 (s), 137.82 (s), 128.48 (s), 126.30 (s), 125.76 (s), 115.39 (d, J=35.1 Hz), 39.30 (s); ESIMS m/z 226.3 ([M+H]$^+$), 224.4 ([M−H]$^−$).

Example 3

Preparation of 5-fluoro-4-imino-3-(trideuteriomethyl)-1H-pyrimidin-2-one (3)

Step 1: 1-(Benzenesulfonyl)-5-fluoro-4-imino-3-(trideuteriomethyl)pyrimidin-2-one. A solution of 4-amino-5-fluoro-1-(phenylsulfonyl)pyrimidin-2(1H)-one (600 mg, 2.23 mmol) (prepared as described in Boebel, T. et al. WO 2011/017547 A) in dimethylformamide (DMF; 7 mL) was treated with lithium carbonate (333 mg. 4.51 mmol) and iodomethane-d$_3$ (807 mg, 5.56 mmol). The reaction mixture was heated at 45° C. for 3.5 h. Ethyl acetate (EtOAc; 10 mL) and saturated aqueous sodium chloride solution (10 mL) were added and the layers separated. The aqueous layer was extracted twice more with EtOAc (2×5 mL). The combined organic layers were washed with saturated aqueous sodium chloride solution (3×5 mL), dried (Na$_2$SO$_4$) and concentrated under reduced pressure. The resulting yellow solid was purified by silica gel chromatography (eluting gradient of 0-80% EtOAc in hexanes) to yield the title compound as a white solid (307 mg, 48%): $^1$H NMR (400 MHz, CDCl$_3$) δ 8.11 (m, 2H); 7.85-7.61 (b, m, 4H); $^{19}$F NMR (375 MHz, CDCl$_3$) δ 158.14; $^{13}$C NMR (100 MHz, CDCl$_3$) δ 152.18, 151.91, 151.64, 142.35, 137.76, 135.56, 129.79, 129.55; ESIMS m/z 287.1 ([M+H]$^+$).

Step 2: 5-Fluoro-4-imino-3-(trideuteriomethyl)-1H-pyrimidin-2-one (3). A solution of 1-(benzenesulfonyl)-5-fluoro-4-imino-3-(trideuteriomethyl)pyrimidin-2-one (360 mg, 1.26 mmol) was dissolved in a mixture of 2,2,2-trifluoroacetic acid (31.9 mmol, 2.4 mL) and dimethyl sulfide (5.9 mmol, 0.57 mL) for 2 h at room temperature and concentrated under reduced pressure. The resulting amorphous gel was purified under reduced pressure and purified by silica gel chromatography (eluting gradient from 0-50% MeOH in dichloromethane). After evaporating the purified product to dryness, it was dissolved in anhydrous methanol (10 mL) and stirred gently for 2 days with 1.5 g of PS-carbonate beads. The product was then collected by vacuum filtration and evaporated to constant mass to yield the title compound as a white solid (59 mg, 40%): $^1H$ NMR (400 MHz, DMSO-$d_6$) δ 7.5 (s, 1H); $^{19}F$ NMR (375 MHz, DMSO-$d_6$) δ 171.45; $^{13}C$ NMR (100 MHz, DMSO-$d_6$) δ 152.18, 151.64, 137.76, 135.56, 129.66; ESIMS m/z 147.2 ($[M+H]^+$).

Example 4

Evaluation of Fungicidal Activity: Leaf Blotch of Wheat (*Mycosphaerella graminicola*; anamorph: *Septoria tritici*; Bayer code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

Example 5

Evaluation of Fungicidal Activity: Apple Scab (*Venturia inaequalis*; Bayer code VENTIN)

Apple seedlings (McIntosh or Golden Delicious) were grown in Metro mix and inoculated with a spore suspension containing 5×105 spore/ml. Plants were placed in a dew room for 24 hours with 100% relative humidity and then transferred to a greenhouse with a temperature of 18° C. for disease to develop.

The following table presents the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

In each case of Table I the rating scale is as follows:

| % Disease Control | Rating |
|---|---|
| 76-100 | A |
| 51-75 | B |
| 26-50 | C |
| 0-25 | D |
| Not Tested | E |

TABLE I

One-Day Protectant (1DP) and Three-Day Curative (3DC) Activity of Compounds on SEPTTR at 100 ppm

| Cmpd | SEPTTR 100 PPM 1DP | SEPTTR 100 PPM 3DC |
|---|---|---|
| 1 | A | A |
| 2 | B | A |
| 3 | D | D |

TABLE II

One-Day Protectant (1DP) Activity of Compound on VENTIN at 100 ppm

| Cmpd | VENTIN 100 PPM 1DP |
|---|---|
| 1 | B |

What is claimed is:

1. A compound of Formula (I):

Formula I 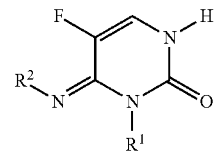 wherein $R^1$ is:

$C_1$-$C_6$ alkyl optionally substituted with 1-3 $R^3$;

$C_1$-$C_6$ alkenyl optionally substituted with 1-3 $R^3$;

$C_3$-$C_6$ alkynyl optionally substituted with 1-3 $R^3$;

phenyl or benzyl wherein each of the phenyl or the benzyl may be optionally substituted with 1-3 $R^4$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^4$, $-(CHR^5)_mOR^6$;

$-C(=O)R^7$;

$-C(=S)R^7$;

$-C(=O)OR^7$;

$-C(=S)OR^7$;

$-S(O)_2R^7$;

$-(CHR^5)_mN(R^8)R^9$;

$-C(=O)N(R^8)R^9$; or $-C(=S)N(R^8)R^9$;

wherein m is an integer 1-3;

$R^2$ is:

H; or $C_1$-$C_6$ alkyl optionally substituted with $R^3$;

$R^3$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, $C_3$-$C_6$ trialkylsilyl, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^4$;

$R^4$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_1$-$C_6$ alkylsulfonyl or $C_2$-$C_6$ alkylcarbonyl, nitro, hydroxyl, or cyano;

$R^5$ is H, $C_1$-$C_6$ alkyl, $C_1$-$C_6$ alkoxy, phenyl or benzyl wherein each of the benzyl or the phenyl may be optionally substituted with 1-3 $R^4$;

$R^6$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^4$, or with a 5- or 6-membered saturated or unsaturated ring system, or with 5-6 fused ring system, or with a 6-6 fused ring system each containing 1-3 heteroatoms wherein each ring may be optionally substituted with 1-3 $R^4$, biphenyl or naphthyl optionally substituted with 1-3 $R^4$;

$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^4$, or with a 5- or 6-membered saturated or unsaturated ring system, or with a 5-6 fused ring system, or 6-6 fused ring system each containing 1-3 heteroatoms wherein each ring may be optionally substituted with 1-3 $R^4$, biphenyl or naphthyl optionally substituted with 1-3 $R^4$;

$R^8$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^4$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^4$, biphenyl or naphthyl optionally substituted with 1-3 $R^4$; and $R^9$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl may be optionally substituted with 1-3 $R^4$;

alternatively $R^8$ and $R^9$ may be taken together to form a 5- or 6-membered saturated or unsaturated ring containing 1-3 heteroatoms wherein each ring may be optionally substituted with 1-3 $R^4$.

2. A composition for the control of a fungal pathogen including the compound of claim 1 and a phytologically acceptable carrier material.

3. The composition of claim 2 wherein the fungal pathogen is at least one of Apple Scab (*Venturia inaequalis*), Leaf Blotch of Wheat (*Septoria tritici*), Leaf Spot of Sugarbeets (*Cercospora beticola*), Leaf Spots of Peanut (*Cercospora arachidicola* and *Cercosporidium personatum*), and Black Sigatoka of Banana (*Mycosphaerella fijiensis*).

4. A method for the control of fungal attack on a plant, the method including the steps of: applying a fungicidally effective amount of at least one of the compounds of claim 1 to at least one of the plant, an area adjacent to the plant, soil adapted to support growth of the plant, a root of the plant, foliage of the plant, and a seed adapted to produce the plant.

* * * * *